United States Patent [19]
Eppler et al.

[11] Patent Number: 6,018,387
[45] Date of Patent: Jan. 25, 2000

[54] DEVICE FOR MEASURING LUMINESCENCE

[75] Inventors: Jörg Eppler, Keltern Dietlingen; Hermann Leistner, Birkenfeld, both of Germany

[73] Assignee: Stratec Electronik GmbH, Germany

[21] Appl. No.: 09/020,985

[22] Filed: Feb. 9, 1998

[51] Int. Cl.[7] .......................... G01N 21/76; G01N 21/63
[52] U.S. Cl. .......................... 356/246; 250/361 C; 422/52
[58] Field of Search ............................. 250/361 C, 458.1, 250/459.1, 462.1; 356/417, 418, 318, 246; 422/52, 55, 58, 82.08, 82.11; 436/47, 72

[56] References Cited

U.S. PATENT DOCUMENTS

| | | | |
|---|---|---|---|
| 4,293,225 | 10/1981 | Wheaton et al. | 356/417 |
| 4,501,970 | 2/1985 | Nelson | 250/458.1 |
| 4,772,453 | 9/1988 | Lisenbee | 422/52 |
| 5,202,091 | 4/1993 | Lisenbee | 422/52 |
| 5,682,232 | 10/1997 | Tajima et al. | 250/361 C |

*Primary Examiner*—Frank G. Font
*Assistant Examiner*—Zandra V. Smith
*Attorney, Agent, or Firm*—Pendorf & Cutliff

[57] ABSTRACT

The invention concerns a measuring device for carrying out of chemiluminescence and/or fluorescence measurements of fluid samples, which in sample containers (22) of a sample plate (24) are contained. For analysis of a measurement light exiting from an upper measurement opening (26) of a sample container (22) found in a measurement position, a photo-multiplier (12) is provided, which for achievement of a flat device construction is provided lying down. In order that the measurement light is redirected into the entry window (36) of the photo-multiplier (12) there is provided a reflector (16) before the photomultiplier (12) in the carrier body (14) which covers over at least the measurement opening (26) of the sample container (22) to be measured, at a distance (FIG. 1).

22 Claims, 3 Drawing Sheets

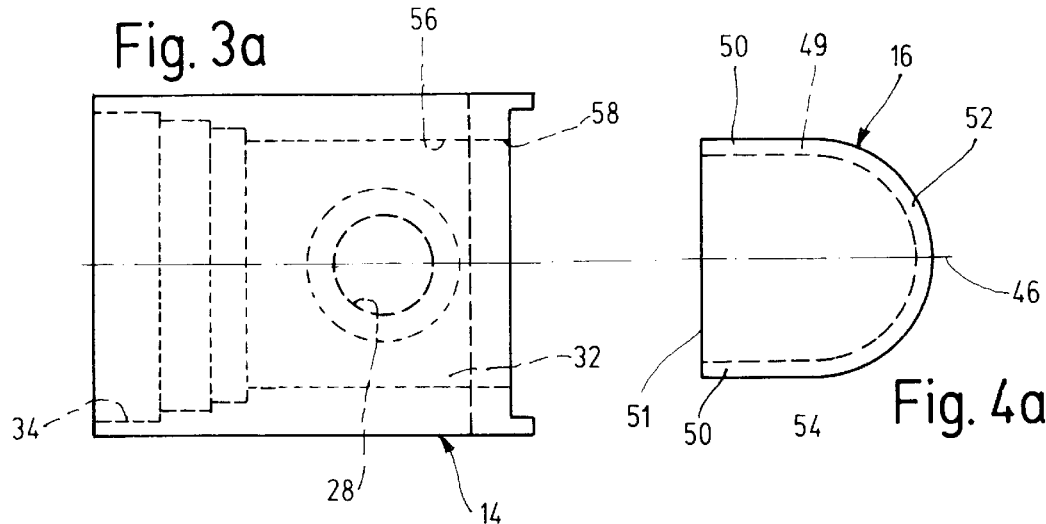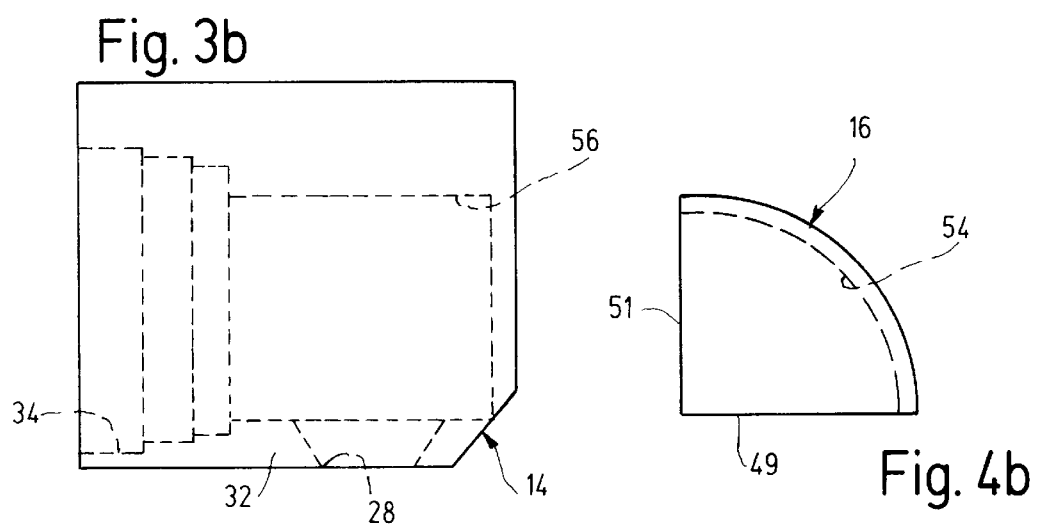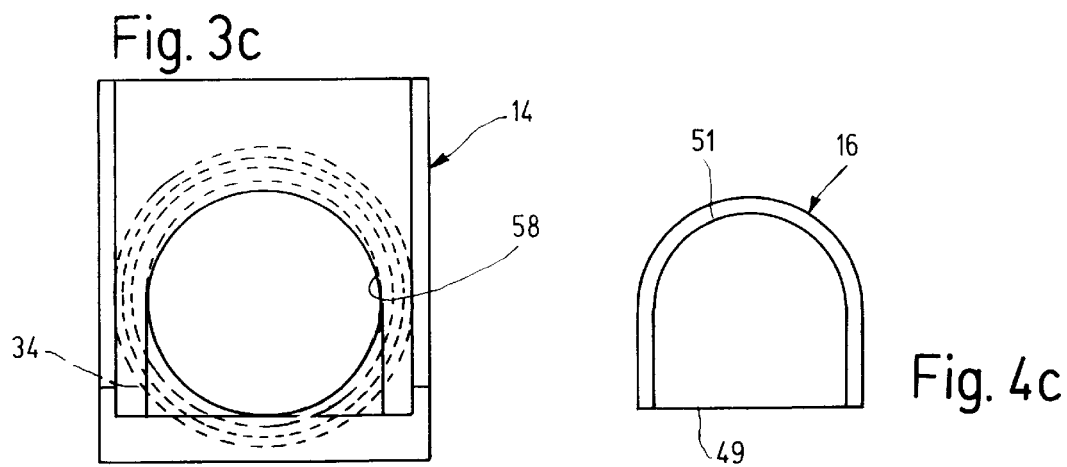

DEVICE FOR MEASURING LUMINESCENCE

BACKGROUND OF THE INVENTION

1. Field of the Invention

The Invention concerns a measuring device for carrying out luminescence measurements, in particular chemiluminescence and/or fluorescence measurements of fluid samples, with a light detector, in particular a photomultiplier for receiving light emitted from an upwardly directed measurement opening of a sample container on an entry surface.

2. Description of the Related Art

Measurement devices of this type are employed above all in chemical, clinical and environmental analysis for research, in which high sensitivity and selectivity for the substances to be detected are necessary. The detection principal is based upon the detection of the light signal, which is emitted from an analyte which has been stimulated by a chemical reaction or by a irradiation with excitation or activation light to chemiluminescence or as the case may be fluorescence emissions. Thereby it is known to measure measurement light emitted from a sample container via a diaphragm with a photo-multiplier, of which the face side entry window is concentric with the sample container opening in the vertical separation to this is provided. As a disadvantage it can be seen that by the vertical upwardly directed longitudinally extending photo-multiplier the construction height of the measurement device is substantially increased. In addition the supporting or mounting of the detector in a vertical position is more difficult.

In order to avoid these problems, it is known with a similar measurement device, that the measurement light is coupled to the measurement opening of an optical fiber, of which the emissions side is coupled to a photo-multiplier. In this manner it is on the one hand possible to avoid limitations in the design of the photo-multiplier, however they occur in the use of a fiber optic besides the worsening of the projection quality, substantial losses in the light yield. Besides this the optical fiber impedes the in certain cases necessary access of additional construction elements in the area of the measurement opening.

SUMMARY OF THE INVENTION

Beginning therefrom, the object of the invention is based thereon of improving the measurement device of the type described in the introductory portion, which makes possible a flat or horizontal apparatus construction with a high detection sensitivity and a flexible measurement process.

The essence of the invention is seen therein, to redirect at least the central bundle of the light emitted upwardly out of the sample chamber by reflection into the entry cross-sectional area of the light detector. This is made possible thereby, that the light is redirected by a reflector which covers over the measurement opening with maintaining empty the interstitial space to the entry surface of the light detector. By the attainable high reflection degree then the major portion of the light to be measured can be detected without there being any disadvantages associated with the orientation of the detector. Also, there can on the basis of the divergent light emission in the in-between space between the measurement opening and the reflector surface spanning over the measurement opening in a simple manner the homogenous imaging of the light emission surface of the sample container upon the generally larger light entry surface of the detector. To this there comes the advantage that construction elements engaging in the interstitial space as necessary for a flexible measure process, in particular for injection of reagents or emission of excitation beams, be provided in an advantageous manner. In a preferred embodiment of the invention the entry surface of the light detector above the sample container is perpendicular to the measurement opening thereof oriented. Therewith it becomes possible to utilize a photo-multiplier as light detector of which the longitudinally extending tube can be provided lying horizontally so that the device can be constructed with an overall low profile. Also a preferred or suitable orientation of the entry surface of the photo-multiplier with respect to the measurement opening offers yet a further advantage in this respect.

Further it is of advantage, when the reflector in a suitable design is so oriented or provided or situated, that the measurement light is redirected as a light bundle, which essentially eliminates the entry surface of the light detector, wherein the central axis of the reflected light bundle is seated perpendicularly upon the entry surface for minimizing the edge ray loss. The reflector can therefore, at least in the area of the measurement opening, be concave, in particularly sphereoidal or parabolic rounded off reflector surface, so that also edge rays are redirected with only one reflection in the axial direction of the light detector.

In order to make possible a homogenous as possible imaging of the light emission surface of the sample container upon the entry surface of the light detector to achieve, the reflector is preferably mirror symmetric to one of the central axis of the receiving and reflected measurement light spanning middle height area formed.

In respect to the construction it is advantageous when the reflector is formed as a deep draw form component. Basically it is however also possible that the reflector as a planer mirror exhibits a planer reflection surface. Thereby it is of advantage for the light transmission when the planer mirror is less than a acute, preferably 45° angle with respect to the measurement opening of the sample container and the entry surface of the light detector is provided tilted.

In order to achieve a high degree of reflection in the spectral area of interest, in particular also blue, the reflector can exhibit a reflector surface formed of an aluminum metal layer or coating. A chemical impairment or interference of the reflector surface can thereby be prevented or minimized, that it is provided with a measurement light transmitting protective layer in particular of silicium dioxide.

In an advantageous construction manner the reflector is capable of being fixed upon a carrying or support body which at the same time shields from stray or foreign light. In order also to prevent the light spilling over between adjacent sample containers, the carrying body may exhibit a diaphragm opening which surrounds about the rim the measurement opening conically and upwardly towards the reflector broadening diaphragm opening. Thereby it is of advantage when the carrying body is seatable upon a bore hull in particular one which via a sealing means against penetration of foreign light is shielded step bore upon the entry side of the photo-multiplier is seatable and is fixably connectable therewith.

According to a further preferred embodiment of the invention the carrying body and/or the reflector exhibits at least one entry or supply canal for receiving a light cable or an optical fiber or a injection conduit formed by a canula or a hose. Therewith it is possible, in the measurement position the light emission of the sample to initiate or release or as the case may be to influence, which is particularly advantageous in a time resolution measurement. In order thereby to keep free the beam path of the measurement light from obstacles, it extends in a entry canal, preferably in a transverse direction to the middle planer height to the reflectors. A suitable engagement position can thereby be achieved, that the free end of the introduction canal guided optical fiber and/or injection channel project into the measurement opening at an angle of 20° to 30° preferably 25° with respect to the vertical to the rim areas of the measurement opening facing away from the middle reflector plane of the reflector.

BRIEF DESCRIPTION OF THE DRAWINGS

In the following the invention will be described in greater detail by reference to the illustrative embodiments shown in schematic manner in the figures. There are shown:

FIG. 3a through 3c A further embodiment of a carrying body in a top view, side view and end view;

FIG. 4a through 4c A reflector capable of being employed in the outer body according to FIG. 3 in a representation corresponding to FIG. 3.

DETAILED DESCRIPTION OF THE INVENTION

Figure 1:
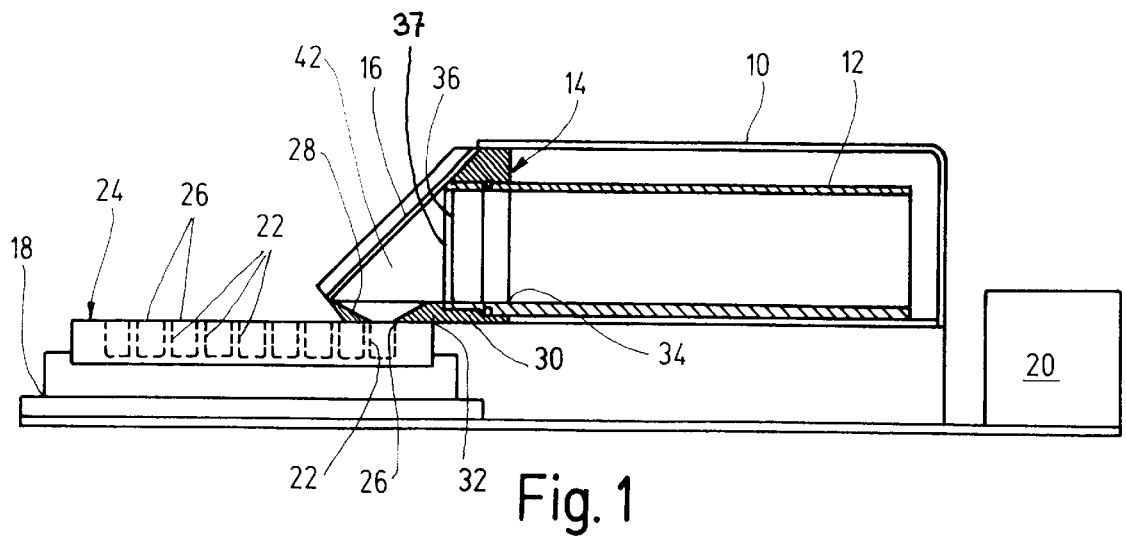
FIG. 1 A measurement device for carrying out of luminescence measurements in a partial sectional side view.

The measuring device shown in the drawing can be employed for chemiluminescence as well also for fluorescence measurements of fluid samples and is comprised essentially of an, in a protective housing 10, horizontally lying arranged photo-multiplier 12, an outer body 14 seated at the entry site of the photo-multiplier, a reflector 16 fixable in the outer body 14 and a positioning device 18, 20 for positioning the sample container 22 of a sample plate 24 in one of the device fixed photo-multiplier 12 associated measurement positions.

The cylindrical sample container 22 of the sample plate 24 constructed as a micro-test plate are provided in a matrix like manner and include an upwardly directed measurement opening 26 through which the luminescence light resulting from a luminescence reaction or a fluorescencing process can be emitted upwardly as measurement light (in short: measurement light). For positioning of the individual sample containers 22 in a measurement position there serves a X-Y-displacement mechanism 18, upon which the sample plate 24 is fixable, and which is automatically operable by means of a drive mechanism 20.

The sample container 22 situated in the measurement position is aligned on its measurement opening 26 with a conically upwardly widening shutter opening 28, which is formed on a diaphragm plate 32 lying flat upon the sample plate 24. The diaphragm plate 32 transitions to a connection piece 30 of the outer body 14, which on a backside face extending step bore 34 upon the appropriate or corresponding cylindrical stepped entry side of the photo-multiplier 12 is seatable upon. The central axis of the step bore 34 cuts through the appropriate or respective axis of the shutter opening 28 perpendicularly. Therewith also the entry surface of the photo-multiplier 12, which is formed by a vertical extending circular entry window 36 perpendicular to the measurement opening 26 of the sample container 22 found in the measurement position is provided. For filtering of excitation and foreign light components in particular during fluorescence excitation an optical filter 37 can be prepositioned in the entry window 36.

Figure 2:
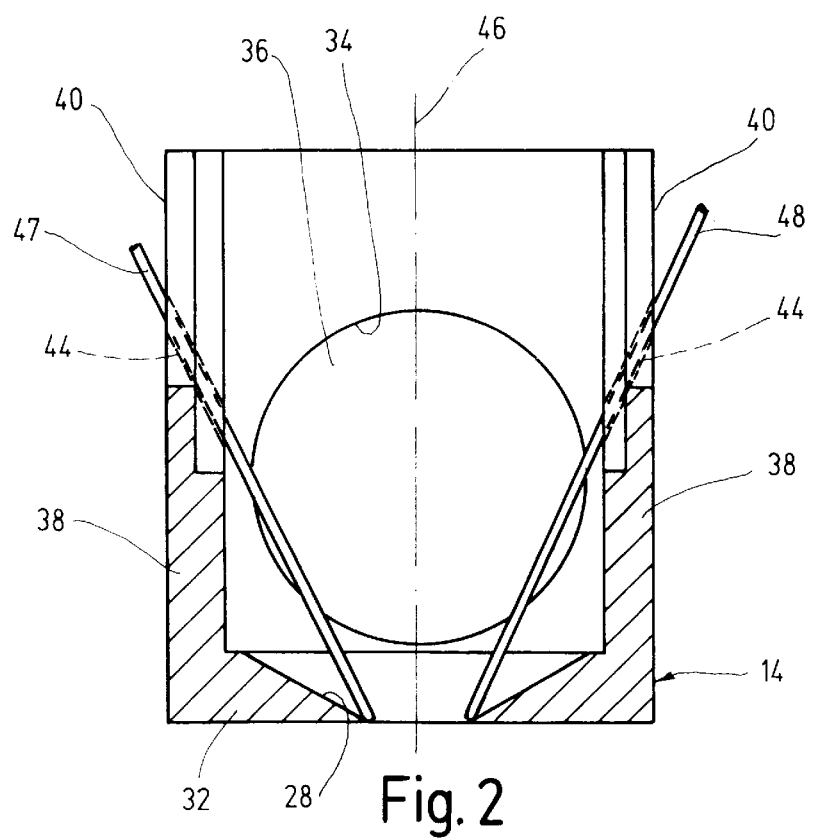
FIG. 2 A carrying body provided at the entry side of a light detector of the measuring device according to FIG. 1, provided with a planer mirror as a reflector in a vertical section.

In the illustrative embodiment showing FIG. 1 and 2, the outer body 14 formed has a single piece of plastic exhibits triangular shaped side walls 38 which extend out sideways or at the sides from the entry window 36 between the diaphragm plate 32 and the connection piece 30. The sidewalls 38 possess a step edge 40 at an angle of 45° perpendicularly arranged to the free side for receiving the reflector 16 which is formed as a right angled planer mirror. The carrying body 14 and the thereupon fixed planer mirror 16 border therewith a reflector space 42 with rims open to the measurement opening 26 and the entry window 36 but in the remainder however, light tight sealed reflector space 42.

The measurement light emitted to the reflector space 42 from the measurement opening 26 is reflected in large proportion at the planer mirror 16 and enters as divergent light bundle through the entry window 36 of the photo-multiplier 12. Thereby there is in the selected arrangement the central beam of the measurement light reflected in the direction of the longitudinal axis of the photo-multiplier 12.

In order to be able to introduce reagents into the measurement position for starting the chemiluminescence or light for fluorescence excitation of the sample in the sample container 22 to be measured, the outer body 14 exhibits introduction canals 44 which extend through the side walls 38 angularly through the median elevated plane 46 of the carrier body 14 or as the case may be the reflector 16. Through the introduction canal 44 a optical fiber 47 and an injection canula 48 is guided to the lower rim edge of the diaphragm opening 28.

Figure 5:
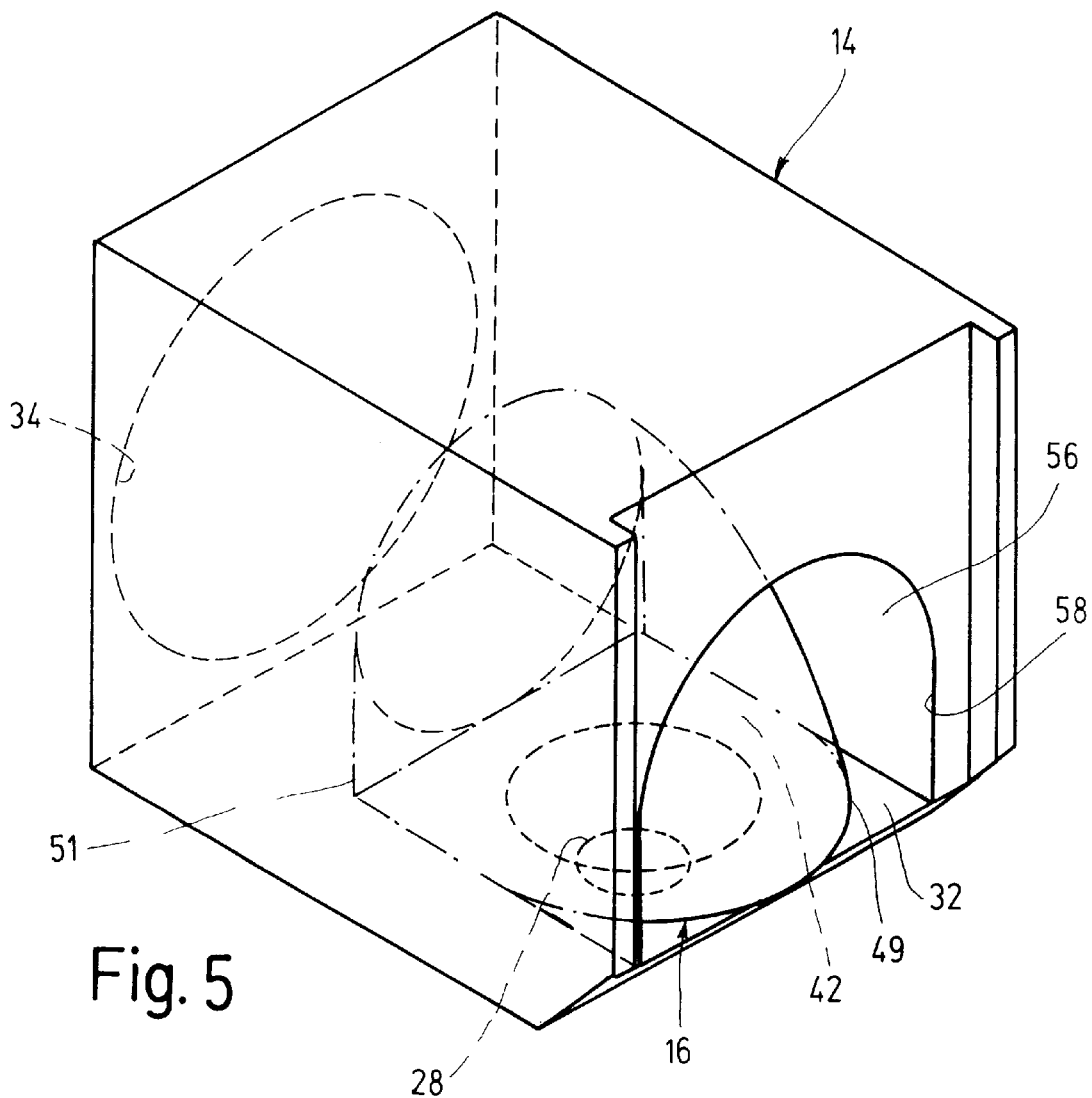
FIG. 5 A outer body according to FIG. 3 with seated reflector according to FIG. 4 in a simplified perspective view.

The illustrative embodiment shown in FIG. 3 through 5 differs from the precedingly described embodiment essentially thereby, that the reflector 16 is formed as a spatially curved form piece and that the carrier body 14 covers and encloses about the outer side of the reflector 16 and thereby protects this from mechanical damage. The reflector 16 showed in various views in FIGS. 4a through 4c essentially possesses the form of a spherical section. The U-shaped end surfaces 49, 51 which are in perpendicular relationship to each other exhibit a ring element 52, on the ends of which two parallel to each other shanks 50 are attached. The shape of the internal space of the reflector 16 produces by a 90° rotation the above-described end surfaces about a through the free end of the shank 50 running axis. On its concave rounded, optically effective reflector surface 54 forming either side the reflector 16 is mirrored by centered or vacuum deposited aluminum and is provided with a supplemental protective layer of centered cords.

The carrying body shown in FIG. 3a through 3c is for its part constructed as one piece of plastic and exhibits the basic shape of a rectangular parallelepiped. For receiving the reflector 16 there is provided a tunnel shaped recess 56 which extends in the extension of the step bore hole 34 to a rim opening 58. The lichte cross section of the recess 56 responds to the outer contour of the end surface 51 of the reflector 16 so that this can be seated inside the opening 58 in the orientation shown in FIG. 5 in the carrier body 14. In the assembled condition the end surface 41, 51 sealed towards downwards to the diaphragm plate 50 and to the end rim border of the step bore shown in simplified manner through its end opening light tight. The reflector 16 and the carrying body 14 in this manner border the reflector space 42 which via the diaphragm opening 28 is open to the sample container and via the step bore 34 to the entry window 36 of the photo-multiplier 12 is open.

By the reflector design and orientation it is achieved, that the central beam of the measurement light exiting from the measurement opening 26 is reflected into the longitudinal axis of the photo-multiplier 12 in the entry window 36 thereof. The rim or edge beams of the measurement light are redirected in the curved reflector surface 54 in an axis approximating direction, so that a small light loss the entry window 36 essentially completely and primarily homogeneously is eliminated by the reflected light beam. Also in this embodiment designed it is envisioned, to introduce injection canulas and/or light fibers through entry canals going through the sides through the carrier body 14 and the reflector 16 let through into the reflector space 42.

In summary the following is to be concluded: The invention concerns a measuring device for carrying out of chemiluminescence and/or fluorescence measurements of fluid samples, which in sample containers 22 of a sample plate 24 are contained. For analysis of a measurement light exiting from an upper measurement opening 26 of a sample container 22 found in a measurement position, a photo-multiplier 12 is provided, which for achievement of a flat device construction is provided lying down. In order that the measurement light is redirected into the entry window 36 of the photo-multiplier 12 there is provided a reflector 16 before the photo-multiplier 12 in the carrier body 14 which covers over at least the measurement opening 26 of the sample container 22 to be measured, at a distance.

We claim:

1. Measurement device for carrying out luminescence measurements of fluid samples, comprising:
    a sample container (22) having an upwardly directed measurement opening;
    a light detector (12) having an entry surface (36) for receiving measurement light emitted from said sample container; and
    a reflector (16) which covers over the measurement opening (26) and, with maintenance of a free space (42), redirects measurement light into the entry surface (36) of the light detector, and wherein the reflector (16) is fixed to a carrier body (14) which shields from stray light.

2. Measurement device according to claim 1, wherein said light detector (12) is a photo-multiplier.

3. Measurement device according to claim 1, wherein the entry surface (36) of the light detector (12) is provided above the sample container (22) and perpendicular to the measurement opening (26).

4. Measurement device according to claim 1, wherein the entry surface (36) of the light detector (12) is provided above the sample container (22) and tilted with respect to the measurement opening (26).

5. Measurement device according to claim 1, wherein the reflector (16) redirects the measurement light as a light bundle into the entry surface (36) so that the central axis of the reflected light bundle enters approximately perpendicular to the entry surface (36).

6. A measurement device according to claim 1, wherein the reflector (16) is formed mirror-symmetrically to a median elevated plane which runs through the central axis of the receiving and reflecting measurement light.

7. Measurement device according to claim 1, wherein the reflector (16) is formed as a deep draw form component.

8. Measurement device according to claim 1, wherein the reflector (16) is a planar mirror exhibiting a planar reflective surface.

9. Measurement device according to claim 8, wherein the planar mirror (16) is oriented tilted at an acute angle with respect to the measurement opening (26) of the sample container (22) and the entry surface (36) of the light detector (12).

10. Measurement device according to claim 8, wherein the planar mirror (16) is oriented at an angle of approximately 45° with respect to the measurement opening (26) of the sample container (22) and the entry surface (36) of the light detector (12).

11. Device according to claim 1, wherein the reflector (16) is provided with a reflector surface (54) formed of a metal layer.

12. Measurement device according to claim 1, wherein the carrier body (14) and/or the reflector (16) exhibits at least one entry channel (44) for receiving an optical fiber (47) or an injection conduit (48) formed by a canula or a hose.

13. Measurement device according to claim 12, wherein at least one entry channel (44) runs transverse to the median elevated plane (46) of the reflector.

14. Measurement device according to claim 13, wherein in the optic fiber (47) and/or injector channel (48) directed in the entry channel extend at an angle of 26° to 30° to the vertical to a rim area of the aperture away from the median elevated plane of the reflector (16).

15. Measurement device for carrying out luminescence measurements of fluid samples, comprising:
    a sample container (22) having an upwardly directed measurement opening;
    a light detector (12) having an entry surface (36) for receiving measurement light emitted from said sample container; and
    a reflector (16) which covers over the measurement opening (26) and, with maintenance of a free space (42), redirects measurement light into the entry surface (36) of the light detector, wherein the reflector (16) in an area above the measurement opening (26) exhibits a concave curved reflector surface (54).

16. Measurement device according to claim 15, wherein said concave curved reflector surface is spheroidic or parabolic.

17. Measurement device for carrying out luminescence measurements of fluid samples, comprising:
- a sample container (22) having an upwardly directed measurement opening;
- a light detector (12) having an entry surface (36) for receiving measurement light emitted from said sample container; and
- a reflector (16) which covers over the measurement opening (26) and, with maintenance of a free space (42), redirects measurement light into the entry surface (36) of the light detector, wherein the reflector (16) is provided with a reflector surface (54) formed of aluminum, and wherein the reflector (16) is fixed to a carrier body (14) which shields from stray light.

18. Measurement device according to claim 17, wherein the reflector surface (54) is provided with a protective layer transparent to measurement light.

19. Measurement device according to claim 18, wherein said protective layer is comprised of $SiO_2$.

20. Measurement device according to claim 17, wherein the carrier body (14) includes an aperture opening which encompasses about the edges of the measurement opening (26), and broadens conically upwardly towards the reflector (16).

21. Measurement device according to claim 20, wherein the carrier body (14) is seatable and in fixed communication with a bore hole (34) and is seatable upon the entry side end of the photo-multiplier (12) an fixedly connected thereto.

22. Measurement device according to claim 20, wherein the bore hole (34) is a step bore shielded from stray light by a shield.

* * * * *

UNITED STATES PATENT AND TRADEMARK OFFICE
CERTIFICATE OF CORRECTION

PATENT NO. : 6,018,387
DATED : January 25, 2000
INVENTOR(S) : Joerg Eppler and Hermann Leistner It is certified that error appears in the above-identified patent and that said Letters Patent is hereby corrected as shown below:

[30] Foreign Application Priority Data
Feb. 7, 1997 [DE] German Pat. Off. .......... 19704731.9

Signed and Sealed this

Tenth Day of October, 2000

Attest:

Q. TODD DICKINSON

*Attesting Officer*    *Director of Patents and Trademarks*